US009744240B2

(12) United States Patent
Guth et al.

(10) Patent No.: US 9,744,240 B2
(45) Date of Patent: Aug. 29, 2017

(54) STORAGE-STABLE DUST-FREE HOMOGENEOUS PARTICULATE FORMULATION COMPRISING AT LEAST ONE WATER-SOLUBLE VITAMIN E-DERIVATIVE AND AT LEAST ONE HYDROPHILIC POLYMER

(71) Applicant: BASF SE, Ludwigshafen (DE)

(72) Inventors: Felicitas Guth, Neustadt (DE); Karl Kolter, Limburgerhof (DE); Michael Schönherr, Frankenthal (DE); Franz Weber, Eppelheim (DE)

(73) Assignee: BASF SE, Ludwigshafen (DE)

( * ) Notice: Subject to any disclaimer, the term of this patent is extended or adjusted under 35 U.S.C. 154(b) by 263 days.

(21) Appl. No.: 14/036,445

(22) Filed: Sep. 25, 2013

(65) Prior Publication Data
US 2014/0086993 A1    Mar. 27, 2014

Related U.S. Application Data

(60) Provisional application No. 61/706,139, filed on Sep. 27, 2012.

(51) Int. Cl.
*A61K 47/00* (2006.01)
*A61K 47/22* (2006.01)
*A61K 47/32* (2006.01)

(52) U.S. Cl.
CPC .............. *A61K 47/22* (2013.01); *A61K 47/32* (2013.01)

(58) Field of Classification Search
CPC ...... A61K 47/22; A61K 47/32; A61K 9/1617; A61K 9/1682
See application file for complete search history.

(56) References Cited

U.S. PATENT DOCUMENTS

| 3,102,078 A | 8/1963 | Robeson |
| 4,603,143 A | 7/1986 | Schmidt |
| 5,179,122 A | 1/1993 | Greene et al. |
| 5,891,469 A | 4/1999 | Amselem |
| 5,891,845 A * | 4/1999 | Myers ........................... 424/451 |
| 6,599,528 B1 | 7/2003 | Rosenberg et al. |
| 2003/0236236 A1 | 12/2003 | Chen |
| 2005/0208082 A1 | 9/2005 | Papas et al. |
| 2006/0057073 A1 * | 3/2006 | Lintz et al. ...................... 424/45 |
| 2006/0198814 A1 * | 9/2006 | Gruening et al. ........... 424/78.3 |
| 2007/0128289 A1 * | 6/2007 | Zhao ............................. 424/489 |
| 2010/0011610 A1 * | 1/2010 | Bittorf et al. ................... 34/359 |
| 2012/0225953 A1 | 9/2012 | Berndl et al. |

FOREIGN PATENT DOCUMENTS

| EP | 1880715 | 1/2008 |
| WO | WO-00/57854 | 10/2000 |
| WO | WO-01/00175 | 1/2001 |
| WO | WO-01/91727 | 12/2001 |
| WO | WO-2005/039551 | 6/2005 |
| WO | WO-2007/019058 | 2/2007 |
| WO | WO-2008/009689 | 1/2008 |
| WO | WO-2009/130204 | 10/2009 |

OTHER PUBLICATIONS

PCT International Search Report in PCT/EP2013/069111, dated Nov. 5, 2013, 4 pgs.
Non-Final Office Action in U.S. Appl. No. 14/036,365, dated Feb. 26, 2014, 11 pages.
Non-Final Office Action in U.S. Appl. No. 14/036,365, dated Oct. 5, 2015, 12 pages.

* cited by examiner

*Primary Examiner* — Robert A Wax
*Assistant Examiner* — Olga V Tcherkasskaya
(74) *Attorney, Agent, or Firm* — Servilla Whitney LLC

(57) ABSTRACT

A storage-stable dust-free homogeneous particulate formulation comprising at least one water-soluble Vitamin E-derivative and at least one hydrophilic polymer. In one embodiment the storage-stable dust-free homogeneous particle formulation, consists of
(a) at least one water-soluble Vitamin E-derivative,
(b) at least one hydrophilic polymer,
(c) optionally additional surface-active substances, and
(d) optionally additional pharmaceutical additives,
with the proviso, that the sum of (a), (b), (c) and (d) equals 100% by weight of the formulation, and wherein the fines fraction with particle diameters of less than 100 µm is less than 10% by weight.
Methods of making the particulate formulation by a spray granulation process are also provided.

20 Claims, No Drawings

STORAGE-STABLE DUST-FREE HOMOGENEOUS PARTICULATE FORMULATION COMPRISING AT LEAST ONE WATER-SOLUBLE VITAMIN E-DERIVATIVE AND AT LEAST ONE HYDROPHILIC POLYMER

CROSS-REFERENCE TO RELATED APPLICATIONS

This application claims the benefit of priority under 35 U.S.C. §119(e) to U.S. Provisional Application No. 61/706,139, filed Sep. 27, 2012, the entire content of which is incorporated herein by reference in its entirety.

BACKGROUND

It is well known in the art that surfactants can be used for enhancing the solubility of hydrophobic active ingredients in an aqueous medium and thus improve bioavailability of the active ingredient.

Among the various surfactants water-soluble vitamin E derivatives are known as potential agents for enhancing solubility. Well known water-soluble Vitamin E-derivative is tocopheryl polyethylene glycol succinates (TPGS). It is known for example from U.S. Pat. No. 3,102,078 that TPGS can be used as a solubilizing agent for fat-soluble vitamins.

Due to its waxy nature TPGS is difficult to handle. Many attempts have been made to overcome this disadvantage.

U.S. Pat. No. 5,179,122 describes a solid composition where TPGS is absorbed or adsorbed to an inert carrier such as microcrystalline cellulose, starch or inorganic materials.

WO 01/00175 discloses mechanically stable pharmaceutical dosage forms which are solid solutions of active ingredients in an auxiliary agent matrix. The matrix contains a homopolymer or a copolymer of N-vinyl pyrrolidone and a liquid or semi-solid surfactant.

WO 01/91727 discloses a self-emulsifying active substance formulation comprising at least one active substance and a formulation basis which includes a lipid component, a binder component and optionally additional auxiliary agents.

WO 00/57854 discloses mechanically stable pharmaceutical dosage forms comprising plastically mouldable, matrix-forming auxiliaries and more than 10 and up to 40% by weight of a surface-active substance with an HLB of between 2 and 18 that is liquid at 20° C., or has a drop point at between 20 and 50° C. The auxiliaries are prepared by spray-drying or melt extrusion.

WO 2005/039551 discloses a solid pharmaceutical dosage form providing improved oral bioavailability for inhibitors of HIV protease. The dosage form comprises a solid dispersion of at least one HIV protease inhibitor and at least one pharmaceutically acceptable water-soluble polymer and at least one pharmaceutically acceptable surfactant, said pharmaceutically acceptable water-soluble polymer having a Tg of at least about 50° C.

US 2005/0208082 discloses a solubilizing composition comprising a mixture of vitamin E, TPGS and linoleic acid.

US 2003/0236236 discloses pharmaceutical compositions for administration of hydrophobic drugs comprising a hydrophobic drug, a vitamin E substance and a surfactant.

WO 2008/009689 discloses a solubilizing composition comprising a polyalkylene glycol derivative of a tocopheryl compound and at least one polyalkylene glycol fatty acid monoester or diester. The composition is obtained by melt-extrusion of the components.

WO 2009/130204 discloses solid compositions comprising permeability improving substances embedded in a water-soluble matrix. The compositions are obtained by normal spray-drying processes.

Known products still do not satisfy the requirements needed for safe and reliable manufacture of pharmaceutical formulations or dosage forms. Because of the tackiness of and relatively high amount of fines the material is not free-flowing tends to block dosage systems and other parts of the machinery. Another disadvantage of known materials is tendency to caking and therefore reduced storage stability. Yet another problem is phase separation of the waxy surfactant and the hydrophilic polymer, either during manufacture of the solubilizing composition or on storage.

The problem of the present invention was to provide a solubilizing composition based on water-soluble vitamin E-derivatives and hydrophilic polymers that is storage stable, dust-free, free of tackiness, free-flowing, easily miscible and offers good processability in the manufacture of pharmaceutical formulations. In addition, organic solvents should be avoided in manufacturing the solubilizing composition, not only because organic solvents are a safety risk, but also to avoid problems with the allowable residual solvents content.

The solution of this problem was to provide a storage-stable dust-free homogeneous particulate composition, consisting of at least one water-soluble Vitamin E-derivative, at least one hydrophilic polymer, optionally additional surface-active substances, and optionally additional pharmaceutical additives, with a fraction of fines passing through a sieve with a mesh size of 100 µm of less than 10-% b.w. The particulate formulation is manufactured by a spray granulation process.

SUMMARY

The invention refers to a storage-stable dust-free homogeneous particulate formulation, consisting of at least one water-soluble Vitamin E-derivative, at least one hydrophilic polymer, optionally additional surface-active substances, and optionally additional pharmaceutical additives, with a fraction of fines passing through a sieve with a mesh size of 100 µm of less than 10-% b.w. In addition the invention refers to a process for manufacturing the formulation and the use as a solubilizing composition in pharmaceutical formulations.

DETAILED DESCRIPTION

The inventive composition is a storage-stable dust-free particulate formulation, consisting of
 (a) at least one water-soluble Vitamin E-derivative,
 (b) at least one hydrophilic polymer,
 (c) optionally additional surface-active substances, and
 (d) optionally additional pharmaceutical additives,
with the proviso, that the sum of (a), (b), (c) and (d) equals 100% by weight of the formulation, and wherein the fines fraction of the particles is less than 10% b.w. of particles with a diameter below 100 µm.

The particulate formulation according to the invention is manufactured by spray granulation process, preferably by a spouted bed spray granulation process. The resulting particles have an onion-like shape.

The average particle size of the particulate formulation as represented by the $D_{0[4,3]}$ value ranges from 200 µm to 1000 µm, preferably 300 to 700 µm, most preferably 400 to 670 µm. The average particle size is measured by laser diffraction and represents the volume average. For all embodiments disclosed herein the bulk densities of the particulate formulations lie in the range of from 0.4 to 0.74, preferably 0.5-0.65. The angle of repose lies in the range of from 25° to 35° Component (a) is a water-soluble vitamin E-derivative, preferably a polyalkylene glycol derivative, most preferably tocopheryl polyethylene glycol succinates. Suitable polyethylene glycol moieties are those with molecular weights of from 300 to 10.000 g/mol, for example PEG 300, PEG 400, PEG 1000, PEG 15000 or PEG 2000. Particularly preferred is a tocopheryl polyethylene glycol 1000 succinate, i.e. a product with a PEG 1000 moiety (TPGS 1000). in water at 20° C. of more than 25% (g/g) at normal pressure in the range of 0.1 MPa.

The amount of component (a) in the particulate formulation can range from 5 to 20% by weight of the composition, preferably 10 to 20% b.w.

Component (b) is selected from the group consisting of homo- or copolymers of an N-vinyl lactame, cellulose derivatives, polyacrylic polymers, polyvinyl alcohols and oligo- and polysaccharides.

According to one preferred embodiment component (b) is a homo- or copolymer of N-vinyl pyrrolidone. Suitable polyvinyl pyrrolidone homopolymers show K values of from 12 to 100, preferably K 12 to 60 (1% b.w. in water). According to this embodiment a most preferred component (b) is a copolymer of N-vinyl pyrrolidone and vinyl acetate, specifically a copolymer obtained from 6 parts of N-vinyl pyrrolidone and 4 parts of vinyl acetate (copovidone). The K value of such a most preferred copolymer lies in the range of from 20 to 40, particularly 25 to 31.

According to another embodiment component (b) is a copolymer of N-vinyl caprolactam, vinyl acetate and polyethylene glycol with K-values in the range of from 25 to 50, preferably in a weight ratio of 57:30:13 with a K-value of 31 to 41 (1% b.w. solution in ethanol), commercially available as Soluplus®, BASF SE.

According to another preferred embodiment component (b) is a polyacrylate. According to this embodiment a most preferred component (b) is a copolymer of ethyl acrylate and methacrylic acid in a ratio of 1:1, commercially available as Kollicoat MAE 30 DP or 100P, or copolymers of methyl methacrylate and methacrylic acid in ratios of 1:1 and 2:1 commercially available as Eudragit L and S, or terpolymers of ethyl acrylate, methyl methacrylate and trimethylammonioethyl methacrylate in ratios of 1:2:0.2 or 1:2:0.1 commercially available as Eudragit RL and RS.

According to another preferred embodiment component (b) is a cellulose derivative, for example hydroxypropyl methyl cellulose acetate succinate, hydroxypropyl methyl cellulose phthalate, cellulose acetate phthalate, cellulose acetate trimellitate, hydroxypropyl methyl cellulose, hydroxypropyl cellulose, hydroxyethyl cellulose, methyl cellulose.

According to another embodiment of the invention the particulate formulation optionally comprises a component (c) selected from the group consisting of polyalkylene glycol fatty acid esters, polyoxyalkylene glycol fatty alcohol ethers, polyoxyalkylene glycols, poloxamers, and polyoxyalkylene glycol glycerides. Another class of suitable components (c) are alkylene glycol fatty acid mono or diesters. Specific examples are polyoxyl 15 hydroxystearate, polyoxyl 40 hydrogenated castor oil, polyethylene glycol with a molecular weight in the range from 300 to 10000, polyoxyethylene stearylether, polyoxyethylene laurylether, polyoxyethylene cetylether.

According to another embodiment the particulate composition optionally comprises a component (d) is selected from the group consisting of antioxidants, chelating agents, colorants, flavours, fillers, stabilizers, preservatives/biocides. Suitable examples are natural or synthetic tocopherols, ascorbic acid, ethylenediaminetetraacetic acid tetrasodium salt, silica, talc, magnesium stearate or butylated hydroxytoluene. A preferred biocide is silver ions. Other suitable preservatives are parahydroxy benzoic acid esters, benzoic acid salts, sorbic acid, benzalkonium chloride, Thiomersal, citric acid and its salts, propionic acid and its salts. Also ethanol or propylene glycol can be used as preservatives in concentrations of more than 15% b.w. of the solution.

The particulate formulations according to the invention consist of
  (a) 5 to 20% b.w. of at least one water-soluble Vitamin E-derivative,
  (b) 80 to 95% b.w. of at least one hydrophilic polymer,
  (c) 0 to 15% b.w. of additional surface-active substances, and
  (d) 0 to 15% b.w. of additional pharmaceutical additives,
with the proviso that the total amount of (a), (b) and optionally (c) and/or (d) equals 100% b.w. of the formulation, and wherein the fines fraction of the particles is less than 10% b.w. of particles with a diameter below 100 µm.

The average particle size of the particulate formulation as represented by the $D_{0[4,3]}$ value ranges from 200 µm to 1000 µm, preferably 300 to 700 µm, most preferably 400 to 670 µm.

Preferred particulate formulations consist of
  (a) 10 to 20% b.w. of at least one water-soluble Vitamin E-derivative,
  (b) 80 to 90% b.w. of at least one hydrophilic polymer,
  (c) 0 to 15% b.w. of additional surface-active substances, and
  (d) 0 to 15% b.w. of additional pharmaceutical additives,
with the proviso, that the sum of (a), (b), (c) and (d) equals 100% by weight of the formulation, and wherein the fines fraction of the particles is less than 10% b.w. of particles with a diameter below 100 µm.

The average particle size of the particulate formulation as represented by the $D_{0[4,3]}$ value ranges from 200 µm to 1000 µm, preferably 300 to 700 µm, most preferably 400 to 670 µm.

According to one preferred embodiment particulate formulations consist of
  a) 10 to 20% b.w. of at least one tocopheryl polyethylene glycol succinate (TPGS)
  (b) 80 to 90% b.w. of at least one hydrophilic polymer,
  (c) 0 to 15% b.w. of additional surface-active substances, and
  (d) 0 to 15% b.w. of additional pharmaceutical additives,
with the proviso, that the sum of (a), (b), (c) and (d) equals 100% by weight of the formulation, and wherein the fines fraction of the particles is less than 10% b.w. of particles with a diameter below 100 µm. According to this embodiment TPGS 1000 is particularly preferred.

The average particle size of the particulate formulation as represented by the $D_{0[4,3]}$ value ranges from 200 µm to 1000 µm, preferably 300 to 700 µm, most preferably 400 to 670 µm.

According to another preferred embodiment particulate formulations consist of
  (a) 10 to 20% b.w. of at least one TPGS,
  (b) 80 to 90% b.w. of a polyacrylate, (c) 0 to 15% b.w. of additional surface-active substances, and (d) 0 to 15% b.w. of additional pharmaceutical additives, with the proviso, that the sum of (a), (b), (c) and (d) equals 100% by weight of the formulation, and wherein the fines fraction of the particles is less than 10% b.w. of particles with a diameter below 100 μm. TPGS is preferably TPGS 1000. A preferred component (b) is a copolymer of ethyl acrylate and methacrylic acid in a ratio of 1:1, or copolymers of methyl methacrylate and methacrylic acid in ratios of 1:1 and 2:1 or terpolymers of ethyl acrylate, methyl methacrylate and trimethylammonioethyl methacrylate in ratios of 1:2:0.2 or 1:2:0.1.

The average particle size of the particulate formulation as represented by the $D_{0[4,3]}$ value ranges from 200 μm to 1000 μm, preferably 300 to 700 μm, most preferably 400 to 670 μm.

According to another preferred embodiment particulate formulations consist of
(a) 10 to 20% b.w. of at least one TPGS,
(b) 80 to 90% b.w. of a cellulose derivative,
(c) 0 to 15% b.w. of additional surface-active substances, and
(d) 0 to 15% b.w. of additional pharmaceutical additives,
with the proviso, that the sum of (a), (b), (c) and (d) equals 100% by weight of the formulation, and wherein the fines fraction of the particles is less than 10% b.w. of particles with a diameter below 100 μm. TPGS is preferably TPGS 1000.

The average particle size of the particulate formulation as represented by the $D_{0[4,3]}$ value ranges from 200 μm to 1000 μm, preferably 300 to 700 μm, most preferably 400 to 670 μm.

According to another preferred embodiment particulate formulations consist of
(a) 10 to 20% b.w. of at least one TPGS,
(b) 80 to 90% b.w. of a copolymer of N-vinyl caprolactam, vinyl acetate and polyethyleneglycol,
(c) 0 to 15% b.w. of additional surface-active substances, and
(d) 0 to 15% b.w. of additional pharmaceutical additives,
with the proviso, that the sum of (a), (b), (c) and (d) equals 100% by weight of the formulation, and wherein the fines fraction of the particles is less than 10% b.w. of particles with a diameter below 100 μm. TPGS is preferably TPGS 1000. Preferably component (b) is a copolymer of N-vinyl caprolactam, vinyl acetate and polyethylene glycol 6000 with K-values in the range of from 25 to 50, preferably in a weight ratio of 57:30:13 with a K-value of 31 to 41 (1% b.w. solution in ethanol).

The average particle size of the particulate formulation as represented by the $D_{0[4,3]}$ value ranges from 200 μm to 1000 μm, preferably 300 to 700 μm, most preferably 400 to 670 μm.

According to another preferred embodiment particulate formulations consist of
(a) 10 to 20% b.w. of at least one TPGS,
(b) 80 to 90% b.w. of a copolymer of N-vinyl pyrrolidone and vinyl acetate,
(c) 0 to 15% b.w. of additional surface-active substances, and
(d) 0 to 15% b.w. of additional pharmaceutical additives,
with the proviso, that the sum of (a), (b), (c) and (d) equals 100% by weight of the formulation, and wherein the fines fraction of the particles is less than 10% b.w. of particles with a diameter below 100 μm. TPGS is preferably TPGS 1000.

The average particle size of the particulate formulation as represented by the $D_{0[4,3]}$ value ranges from 200 μm to 1000 μm, preferably 300 to 700 μm, most preferably 400 to 670 μm.

A particularly preferred embodiment relates to a particulate formulation consisting of
(a) 10 to 15% b.w. of at least one TPGS,
(b) 85 to 90% b.w. of a copolymer of N-Vinyl pyrrolidone and vinyl acetate,
(c) 0 to 15% b.w. of additional surface-active substances, and
(d) 0 to 15% b.w. of additional pharmaceutical additives,
with the proviso, that the sum of (a), (b), (c) and (d) equals 100% by weight of the formulation, and wherein the fines fraction of the particles is less than 10% b.w. of particles with a diameter below 100 μm. According to this preferred embodiment component (b) preferably is obtained from 6 parts of N-vinyl pyrrolidone and 4 parts of vinyl acetate. TPGS is preferably TPGS 1000.

The average particle size of the particulate formulation as represented by the $D_{0[4,3]}$ value ranges from 200 μm to 1000 μm, preferably 300 to 700 μm, most preferably 400 to 670 μm.

Independently of which of the above described embodiments is chosen for the inventive particulate formulations, the formulations do not comprise a pharmaceutically active ingredient. The vitamin E derivative used according to the invention is used as a surfactant, but it can also serve as an active ingredient. Insofar the statement that the particulate formulations "do not comprise pharmaceutically active ingredient" means no pharmaceutically active ingredient other than the water-soluble vitamin E derivative.

The inventive particulate formulation is not a physical mixture of the components, but a formulated composition wherein the components cannot be separated from each other by mechanical process, such as for instance sieving.

The spray granulation process for manufacturing a particulate formulation according to the invention consisting of
(a) 5 to 20% b.w. of at least one water-soluble Vitamin E-derivative,
(b) 80 to 95% b.w. of at least one hydrophilic polymer,
(c) 0 to 15% b.w. of additional surface-active substances, and
(d) 0 to 15% b.w. of additional pharmaceutical additives,
with the proviso that the total amount of (a), (b) and optionally (c) and/or (d) equals 100% b.w. of the formulation, with a the content of fines fraction with a diameter below 100 μm of less than 10% b.w. of the formulation, is characterized by the following steps:
(i) forming an aqueous solution of components (a), (b) and optionally (c) and (d),
(ii) atomizing said solution with the help of one or more spray nozzles and contacting the atomized solution with a fluidized bed of fines of a particulate material consisting of components (a), (b) and optionally (c) and (d),
(iii) separation of the granulated product from fines with a diameter of less than 100 μm particle size, and
(iv) recirculation of fines into the apparatus.

Step (i): Formation of the Spray Solution

Method (i) a): According to one embodiment of the invention step (i), i.e. the formation of the aqueous spray solution, is carried out in such a way that first of all component (a) is dissolved in water at elevated temperatures followed by blending in the solid hydrophilic polymer into the first solution. Optionally components (c) and (d) are also blended into the first solution. "Elevated temperatures"

means 30 to 60° C., preferably 37 to 55° C. Preferably the dissolution of the components is carried out under stirring.

Method (i) b): According to another embodiment the aqueous spray solution is prepared by dissolving the hydrophilic polymer at ambient temperatures in water and blending in component (a) in solid form. The blending in is preferably carried out under stirring. Optionally the blending in of component (a) can be carried out at elevated temperatures of from 30 to 60° C., preferably 37 to 55° C.

Method (i) c): According to another embodiment component (a) is molten and blended into an aqueous solution of the hydrophilic polymer. The melting of component (a) can be carried out a 40 to 75° C., preferably at 55 to 65° C. Blending in the melt is preferably carried out under stirring.

Method (i) d): According to yet another embodiment a first solution of component (a) is formed at ambient temperatures or preferably at the above mentioned (Method (i) a) or b)) elevated temperatures. A second separate aqueous solution of the hydrophilic polymer is formed. The second solution can be formed at ambient temperatures. The resulting spray solution can be formed in a batch process either by blending in the first solution of component (a) into the second solution or by blending in the second solution into the first solution.

Method (i) e): The first and the second solution can also be blended in a continuous process, for instance by mixing a stream of the first solution with a stream of the second solution in a continuous mixing chamber.

Blending an aqueous solution of the hydrophilic polymer (b) into an aqueous solution of component (a) as described in connection with Method (i) d) is particularly preferred.

Independently of which of the Methods (i) a), b), c), d) or e) is used, the following conditions apply and can be combined where applicable:

The solids content of the spray solution can vary from 10 to 50% b.w., preferably 20 to 40% b.w., particularly 20 to 35% b.w.

The concentration of the vitamin E derivative in the aqueous solution can range from 5 to 22% b.w., preferably 8 to 19% b.w. and most preferred 9-17% b.w.

Additional components such as the optional components (c) or (d) can be blended into the readymade spray solution comprising components (a) and (b) as such or in the form of an aqueous solution or dispersion.

The so formed clear aqueous solution is preferably kept under stirring before being introduced into the fluidized bed spray-granulation apparatus According to another embodiment the solution is kept at elevated temperatures at from 40 to 60° C. According to yet another embodiment the prepared solution is kept under stirring and elevated temperatures of from 40 to 60° C.

Step (ii): Spray Granulation

The spray granulation process is carried out as a fluidized bed spray granulation process. The spray solution obtained in accordance with either of the methods of step (i) is introduced into a fluidized bed spray apparatus, atomized with the help of nozzles and brought in contact with a fluidized bed of fines comprising component (a), (b), and optionally components (c) and (or (d).

Initial nuclei for starting the fluidized bed can be obtained by a spray-drying process. The fines used for building up the fluidized bed usually have a diameter below 100 µm.

New fines can preferably be obtained by an external grinding-classification circuit.

According to this embodiment, the creation of nuclei and discharge of the desired particulate formulation can be controlled by an air-classifying discharge in a such way, that the creation of nuclei and discharge of the granules will occur in a self-regulating equilibrium.

Preferably, the spray nozzles for introducing the spray solution are positioned close to or within the fluidized bed. "Close to" means that the distance from the nozzle to the fluidized bed is such that the atomized spray solution is still in the form of droplets upon contact with the fluidized bed. The spray nozzles may have a direction of spray perpendicular to and/or preferably parallel to the product flow.

By this spray granulation process layer after layer of the solids of the spray solution is deposited on a particle. The resulting particles have a distinctive onion-like structure. Particle size distribution is narrow and the content of fines with a diameter below 100 µm is low (smaller than 10% b.w.).

According to a preferred embodiment the inventive particulate formulation is obtained by a spouted bed granulation process. A spouted bed spray granulation process is a specific embodiment of a fluidized bed spray granulation process. Due to high velocity of the incoming fluidizing gas stream (jet stream) from the bottom of the apparatus the particle movement will be annular. The incoming gas stream of the drying gas is introduced into the apparatus through rectangular slot-like openings at the bottom of the apparatus. The particles will flow upwards through the fluidized bed. The particles are entrained to the top of the bed and then flow downward in the surrounding annulus countercurrently to the gas flow to be flown up again in the next circle.

The equipment for such a process is commercially available for instance under the trade name ProCell by Glatt GmbH.

Independently of which embodiment is used the following conditions for spray granulation apply:

The drying gas can be air, nitrogen or any other inert gas, preferably air is used as drying gas. The drying gas is usually introduced at the bottom of the apparatus through a rectangular slot. The amount of gas flow depends on the dimensions of the apparatus. The temperature of the drying gas usually lies in the range of 80 to 150° C. for the inlet temperature. The outlet temperature lies in the range of 30 to 90, preferably 40 to 60° C.

Spraying of the spray solution can be performed with nozzles such as one, two or three component nozzles, preferably two component nozzles.

The gas flow depends on the dimensions of the apparatus. Typical flow velocities of the drying gas in the rectangular slot are 10 to 50 m/s, preferably 20 to 30 m/s.

According to a preferred embodiment the spray granulation process for manufacturing a particulate formulation consisting of (a) 10 to 20% b.w. of at least one water-soluble TPGS,
(b) 80 to 95% b.w. of at least one hydrophilic polymer,
(c) 0 to 15% b.w. of additional surface-active substances, and
(d) 0 to 15% b.w. of additional pharmaceutical additives, with the proviso that the total amount of (a), (b) and optionally (c) and/or (d) equals 100% b.w. of the formulation, with a the content of fines fraction with a diameter below 100 µm of less than 10% b.w. of the formulation, is characterized by the following steps:

(i) forming an aqueous solution of components (a), (b) and optionally (c) and (d),
(ii) atomizing said solution with the help of one or more spray nozzles and contacting the atomized solution with a fluidized bed of fines of a particulate material consisting of components (a), (b) and optionally (c) and (d), (iii) separation of the granulated product from fines with a diameter of less than 100 µm particle size, and
(iv) recirculation of fines into the apparatus.

According to another preferred embodiment the spray granulation process for manufacturing a particulate formulation according to the invention consisting of
(a) 10 to 20% b.w. of at least one water-soluble TPGS,
(b) 80 to 95% b.w. of a copolymer of N-Vinyl pyrrolidone and vinyl acetate,
(c) 0 to 15% b.w. of additional surface-active substances, and
(d) 0 to 15% b.w. of additional pharmaceutical additives,
with the proviso that the total amount of (a), (b) and optionally (c) and/or (d) equals 100% b.w. of the formulation, with a the content of fines fraction with a diameter below 100 µm of less than 10% b.w. of the formulation, is characterized by the following steps:
(i) forming an aqueous solution of components (a), (b) and optionally (c) and (d),
(ii) atomizing said solution with the help of one or more spray nozzles and contacting the atomized solution with a spouted bed of fines of a particulate material consisting of components (a), (b) and optionally (c) and (d),
(iii) separation of the granulated product from fines with a diameter of less than 100 µm particle size, and
(iv) recirculation of fines into the apparatus. Preferably component (b) is a copolymer of N-vinyl pyrrolidone and vinyl acetate 6:4. Preferably TPGS is TPGS 1000.

Particularly preferred is a combination of this embodiment with Method (i) d) of step (i).

According to another preferred spray granulation process for manufacturing a particulate formulation according to the invention consisting of
(a) 10 to 20% b.w. of at least one water-soluble TPGS,
(b) 80 to 95% b.w. of at least one polyacrylate,
(c) 0 to 15% b.w. of additional surface-active substances, and
(d) 0 to 15% b.w. of additional pharmaceutical additives,
with the proviso that the total amount of (a), (b) and optionally (c) and/or (d) equals 100% b.w. of the formulation, with a the content of fines fraction with a diameter below 100 µm of less than 10% b.w. of the formulation, is characterized by the following steps:
(i) forming an aqueous solution of components (a), (b) and optionally (c) and (d),
(ii) atomizing said solution with the help of one or more spray nozzles and contacting the atomized solution with a fluidized bed or spouted bed of fines of a particulate material consisting of components (a), (b) and optionally (c) and (d),
(iii) separation of the granulated product from fines with a diameter of less than 100 µm particle size, and
(iv) recirculation of fines into the apparatus. Most preferred polyacrylates are described above.

According to another preferred spray granulation process for manufacturing a particulate formulation according to the invention consisting of
(a) 10 to 20% b.w. of at least one water-soluble TPGS,
(b) 80 to 95% b.w. of at least one cellulose derivative,
(c) 0 to 15% b.w. of additional surface-active substances, and
(d) 0 to 15% b.w. of additional pharmaceutical additives,
with the proviso that the total amount of (a), (b) and optionally (c) and/or (d) equals 100% b.w. of the formulation, with a the content of fines fraction with a diameter below 100 µm of less than 10% b.w. of the formulation, is characterized by the following steps:
(i) forming an aqueous solution of components (a), (b) and optionally (c) and (d),
(ii) atomizing said solution with the help of one or more spray nozzles and contacting the atomized solution with a fluidized bed or spouted bed of fines of a particulate material consisting of components (a), (b) and optionally (c) and (d),
(iii) separation of the granulated product from fines with a diameter of less than 100 µm particle size, and
(iv) recirculation of fines into the apparatus. Preferred cellulose derivatives are HPMC or HPMCAS:

The resulting inventive particulate formulation is stable in the packaging on storage even at elevated temperatures such as 40° C. for at least three months.

Formulations according to any of the inventive embodiment can be tested for stability by measuring the firmness of the stored material in a water-tight packaging with a penetrometer. The penetrometer test measures the force necessary for pressing a cone under defined conditions into the stored packaged material. This test can be useful for controlling storage stability of a given packaged material.

After four weeks of storage at 40° C. and 10% relative humidity the firmness of the material stored in water-tight packaging should be less than 1 N measured by 6 mm cone penetrometer. The firmness measured by using a 12 mm cone penetrometer should be <4 N.

The inventive particulate formulation can be used to give pharmaceutical formulations or dosage forms by processing the particulate formulation together with one or more pharmaceutically active ingredients and optionally other excipients or additives.

One method for processing the inventive particulate formulation together with other ingredients to give a pharmaceutical formulation or dosage form is the melt-extrusion process. The melt-extrusion process comprises the steps of preparing a homogeneous melt of the active ingredient or the combination of active ingredients, the pharmaceutically acceptable polymer and the inventive particulate formulation, and cooling the melt until it solidifies. "Melting" means a transition into a liquid or rubbery state in which it is possible for one component to become homogeneously embedded in the other. Typically, one component will melt and the other components will dissolve in the melt, thus forming a solution. Melting usually involves heating above the softening point of the pharmaceutically acceptable polymer. The preparation of the melt can take place in a variety of ways. The mixing of the components can take place before, during or after the formation of the melt. For example, the components can be mixed first and then melted or simultaneously mixed and melted. Usually, the melt is homogenized in order to disperse the active ingredients efficiently. Also, it may be convenient first to melt the inventive particulate formulation and then to admix and homogenize the active ingredients.

Usually, the melt temperature is in the range of 100 to 350° C., preferably 100 to 300° C. However, depending on the nature of the active ingredient or further components present during melt extrusion the temperature range can vary in such a way that the melt temperature can be chosen below 100° C. This might be the case for instance for active ingredients with plastifying properties such as ibuprofen or in the presence of any other plasticize.

According to another embodiment the melt temperature can be lowered by temporary addition of plasticizer such as supercritical carbon dioxide, water or other volatile compounds such as organic solvents, for instance ethanol or isopropanol.

The active ingredients can be employed as such or as a solution or dispersion in a suitable solvent such as alcohols, aliphatic hydrocarbons or esters. Another solvent which can be used is liquid carbon dioxide. The solvent is removed, e.g. evaporated, upon preparation of the melt. Various additives may be included in the melt, for example flow regulators such as colloidal silica; lubricants, bulking agents (fillers), disintegrants, plasticizers, stabilizers such as antioxidants, light stabilizers, radical scavengers, or stabilizers against microbial attack. The melting and/or mixing takes place in an apparatus customary for this purpose. Particularly suitable are extruders or kneaders. Suitable extruders include single screw extruders, intermeshing screw extruders or else multiscrew extruders, preferably twin screw extruders, which can be co-rotating or counter-rotating and, optionally, equipped with kneading disks or other screw elements for mixing or dispersing the melt. The working temperatures will also be determined by the kind of extruder or the kind of configuration within the extruder used. Part of the energy needed to melt, mix and dissolve the components in the extruder can be provided by heating elements. However, the friction and shearing of the material in the extruder may also provide a substantial amount of energy to the mixture and aid in the formation of a homogeneous melt of the components.

The extrudate leaving the extruder ranges from pasty to viscous. Before allowing the extrudate to solidify, the extrudate may be directly shaped into virtually any desired shape. Shaping of the extrudate may be conveniently carried out by a calender with two counter-rotating rollers with mutually matching depressions on their surface. Another option is to form films by calendering. Alternatively, the extrudate is moulded into the desired shape by injection-moulding. Alternatively, the extrudate is subjected to profile extrusion and cut into pieces, either before (hot-cut) or after solidification (cold-cut). Additionally, foams can be formed if the extrudate contains a propellant such as a gas, e.g. carbon dioxide, or a volatile compound, e.g. a low molecular-weight hydrocarbon, or a compound that is thermally decomposable to a gas. The propellant is dissolved in the extrudate under the relatively high pressure conditions within the extruder and, when the extrudate emerges from the extruder die, the pressure is suddenly released. Optionally, the resulting solid solution product is milled or ground to granules. The granules may then be filled into capsules or may be compacted. Compacting means a process whereby a powder mass comprising the granules is densified under high pressure in order to obtain a compact with low porosity, e.g. a tablet. Compression of the powder mass is usually done in a tablet press, more specifically in a steel die between two moving punches.

At least one additive selected from flow regulators, disintegrants, bulking agents (fillers) and lubricants is preferably used in compacting the granules. Disintegrants promote a rapid disintegration of the compact in the stomach and keep the liberated granules separate from one another. Suitable disintegrants are crosslinked polymers such as crosslinked polyvinyl pyrrolidone and crosslinked sodium carboxymethyl cellulose. Another suitable class of disintegrants are sodium starch glycolates (Primojel®).

Suitable bulking agents (also referred to as "fillers") are selected from lactose, calcium hydrogenphosphate, microcrystalline cellulose (Avicel®), magnesium oxide, potato or corn starch, isomalt. Suitable flow regulators are selected from highly dispersed silica (Aerosil®), and animal or vegetable fats or waxes.

A lubricant is preferably used in compacting the granules. Suitable lubricants are selected from polyethylene glycol (e.g., having a Mw of from 1000 to 6000), magnesium and calcium stearates, sodium stearyl fumarate, talc and the like.

Alternatively the particulate formulation according to the invention can be formulated with other pharmaceutical ingredients by a melt-granulation process. In a melt granulation process the material is not converted to a homogeneous melt. The material is only heated to the extent that the surface of the inventive particulate formulation is molten so that the particles get tacky and start to adhere together. The melt granulation process can be carried out in a high-shear mixer or in an extruder which is operated without a die system. Since the extruder is in this case operated with an open discharge no pressure is build up within the extruder.

Alternatively the particulate formulation according to the invention can be formulated with other pharmaceutical ingredients by a wet granulation process or be used in a drug layering process.

The inventive particulate formulations are particularly suitable for preparing pharmaceutical dosage forms comprising active ingredients with a solubility in water of less than 0.1% (g/g), preferably less than 0.01% (g/g) at 20° C. and normal pressure.

The active ingredients may come from any range of indications.

Non-limiting examples which may be mentioned here are benzodiazepines, antihypertensives, vitamins, cytostatics—especially Taxol, anesthetics, neuroleptics, antidepressants, agents having antiviral activity, such as, for example, agents having anti-HIV activity, antibiotics, antimycotics, antidementia agents, fungicides, chemotherapeutics, urologicals, platelet aggregation inhibitors, sulfonamides, spasmolytics, hormones, immunoglobulins, sera, thyroid therapeutics, psychoactive drugs, antiparkinson agents and other antihyperkinetics, ophthalmologicals, neuropathy products, calcium metabolism regulators, muscle relaxants, anesthetics, lipid-lowering agents, hepatotherapeutics, coronary agents, cardiac agents, immunotherapeutics, regulatory peptides and their inhibitors, hypnotics, sedatives, gynecologicals, gout remedies, fibrinolytics, enzyme products and transport proteins, enzyme inhibitors, emetics, blood flow stimulators, diuretics, diagnostic aids, corticoids, cholinergics, biliary therapeutics, anti asthmatics, bronchodilators, beta-receptor blockers, calcium antagonists, ACE inhibitors, arteriosclerosis remedies, antiinflammatory drugs, anticoagulants, antihypertensives, antihypoglycemics, antihypertensives, antifibrinolytics, antiepileptics, antiemetics, antidotes, antidiabetics, antiarrhythmics, antianemics, antiallergics, anthelmintics, analgesics, analeptics, aldosterone antagonists, slimming agents.

The inventive formulations are characterized by an excellent flowability which is even maintained when storing the material at elevated temperatures (40° C.) for at least three months in the humidity-tight packaging. Usually soft materials and in particular materials with a small particle size of more than 10% b.w. below 100 μm show stickiness and cold flow behavior preventing it from a good flowability. Even though the particles of the inventive formulation are characterized by an extremely smooth surface, the particles do not stick together. The angle of repose is below 35°.

The bulk density of the inventive formula is $>0.4$ g/cm$^3$, preferably $>0.50$ g/cm$^3$ and most preferably $>0.55$ g/cm$^3$.

The upper limit of bulk density is 0.74 g/cm³. Normal spray dried powders have bulk density between 0.2 and 0.3 g/cm³.

It was particularly unexpected that the formulations could be processed under the conditions of a fluidized bed or spouted bed spray granulation. In view of the tackiness of the material it was to be expected that the material would adhere to the walls of the granulation apparatus, thus causing great losses of material.

Surprisingly, the throughput rate of the extruder can be adjusted to extremely high values. Thus, on a 16 mm extruder at 200 rpm and a temperature of 150° C. more than 7 kg/h can be run, by far higher than the rates of the single components (Single components can be extruded on a 16 mm extruder at 200 rpm and a temperature of 160° C. only with less than 4 kg/h).

Surprisingly, the inventive formulations do not lead to any dust formation. The amount of fine particles with a size of <100 μm is below 10%. Normally spray dried products have at least 50% of fines below 100 μm. The inventive formulations are also suitable for being filled into capsules. Surprisingly, the filling step can be performed quickly. Normally, soft materials are cohesive so that particles stick together and flow into small openings is hindered.

EXAMPLES

The following methods can be used to characterize the physical properties of the particulate formulations.

Particle Size

The analysis is performed with a Malvern Mastersizer 2000 Vers 5.22, Malvern Instruments, UK). The product is put on the sample plate (vibration intensity 100%) and dispersed with air a pressure of 0.05 MPa. The measurement is carried out with an obscuration between 3-10%

Bulk Density:

The bulk density is the ratio of mass of an untapped powder sample to its volume. The powder is poured into a measuring cylinder of 150 ml and excess powder is discarded with a spatula. The mass of 150 ml Powder is obtained by differential weighing.

Angle of Repose:

The angle of repose is a characteristic related to resistance to movement between particles. It is the constant, three dimensional angle (relative to the horizontal base) assumed by a cone-like pile of material that is formed by draining excess quantity through a funnel by the method described below.

150 ml of untapped powder is filled into a measuring cylinder of 150 ml and excess powder is discarded with a spatula. The powder poured into a funnel (Pfrengle type, diameter 1 cm), of which the opening is closed. The powder is drained from the funnel (if necessary under stirring with 1 rps) to a plate (diameter 10 cm, height 2.5 cm). The angle of repose is calculated from the relation of the height of the powder pile and the radius of the plate.

Sieve Analysis

The degree of fineness of a powder can be expressed by reference to a sieve.

The sieve analysis is performed with an Retsch AS 200 control sieving machine (100 g powder; amplitude: 1.0; sieving time: 10 min, without sieving aids or interruption). Separated fractions are determined by differential weighing.

Example 1

Formulation Comprising 15% b.w. TPGS 1000

62 kg water were heated to a temperature of 50° C. 9 kg molten TPGS (Temperature 60° C.) are added under gentle stirring at low intensity (paddle, 250 rpm) and continuous heating (50° C.) with a paddle stirrer. The stirrer was covered by the solution to avoid foaming. After 60 minutes of stirring TPGS was completely dissolved. 138 kg Copovidon solution with a solid content of 37% b.w. were added under gentle stirring. The mixture was stirred for 15 minutes. The resulting solution was clear and transferred under continuous stirring to the spray granulation apparatus.

Spray granulation was carried out by spouted bed granulation:

| Apparatus | Procell 5 (Glatt) |
|---|---|
| Solid content of the suspension | 30% b.w. |
| Temperature of the gas, inlet | 115° C. |
| Temperature exhaust air | 60° C. |
| Amount of drying gas | 200 m³/h |
| Nozzle gas of the two liquid nozzle | 10 m³/h |
| Flow rate of solution | 5.95 kg/h |

Example 2

Formulation Comprising 10% b.w. TPGS 1000

54 kg water were heated to a temperature of 50° C. 6 kg molten TPGS (Temperature 60° C.) were added under gentle stirring (paddle, 250 rpm) and continuous heating (50° C.) with a paddle stirrer. The stirrer was covered by the solution to avoid foaming. After 60 minutes of stirring TPGS was completely dissolved. 146 kg Copovidon Solution with a solid content of 37% are added under gentle stirring. The mixture was stirred for 15 minutes. The resulting solution was clear and transferred under continuous stirring to the spray granulation apparatus.

Spray granulation was carried out by spouted bed granulation:

| Apparatus | Procell 5 (Glatt) |
|---|---|
| Solid content of the solution | 30% b.w. |
| Temperature of the gas, inlet | 110° C. |
| Temperature exhaust air | 60° C. |
| Amount of drying gas | 200 m³/h |
| Nozzle gas of the two liquid nozzle | 12.7 m³/h |
| Flow rate of solution | 3.50 kg/h |

Comparative Example A

Preparation of a Spray Dried Product

A spray solution according to Example 1 was introduced into a spray drying apparatus with two component nozzles. The solution was sprayed under the following conditions:

| Apparatus | Nubilosa spray tower, height 12 m, diameter 0.8 m |
|---|---|
| Solid content of the solution | 25% b.w. |
| Temperature of the gas, inlet | 115° C. |
| Temperature exhaust air | 55° C. |
| Amount of drying gas | 450 kg/h |
| Pressure of nozzle gas | 0.18 MPa |
| Flow rate of solution | 6.5 kg/h |

Particle sizes: d(0,1): 30 μm; d(0,5): 83 μm; d(0,9): 168 μm D[4,3]: 93 μm

An angle of repose could not be measured due to the poor flowability of the product.

The average particle sizes of the products according to Example 1 and 2 and Comparative Example A were measured as described above. The results are depicted in Table I.

TABLE I

| Process | D(0.1) [μm] | D(0.5) [μm] | D(0.9) [μm] | D0(4.3) [μm] |
|---|---|---|---|---|
| Spray Granulation, Ex. 1 | 382 | 618 | 999 | 659 |
| Spray Granulation, Ex. 2 | 278 | 513 | 893 | 533 |
| Spray-Drying, Comp. Ex. A | 30 | 83 | 168 | 93 |

The firmness of the products according to Examples 1 and 2 and Comparative Example A was determined with a cone penetrometer as described above. The results are depicted in Table II below.

Test Method Penetrometer

The particulate material according to the invention was packed into aluminum foil laminated polyethylene in liner bags (100 μm) of size DIN A 5. The bags were stored in a climate chamber with a relative humidity of 10% either at 30° C. or 40° C. for 10 days, 4 weeks, 8 weeks. The bags were stored with a compression load of 2.2 kPa. After the pre-determined storage time the bags were opened in such a way that the compressed material remains undisturbed.

The firmness of the material was tested with a 6 mm or 12 mm cone tipped penetrometer by determining the force (in [N]) needed to insert the cone for 6 mm or 12 mm into the material.

The penetrometer used according to the examples was a digital mobile force meter PCE-FM 200, PCE Deutschland GmbH.

TABLE II

Storage Stability, Cone Penetrometer Test, Firmness in [N]

| | 10% TPGS | 15% TPGS | Comp. Ex. A |
|---|---|---|---|
| 10 days, 30° C., 6 mm cone | 0.01 | 0.03 | — |
| 10 day, 30° C., 12 mm cone | 0.28 | 0.24 | — |
| 4 weeks, 30° C., 6 mm cone [N] | 0.0 | 0.06 | — |
| 4 weeks, 40° C., 6 mm cone [N] | 0.39 | 0.33 | 2.0 |
| 4 weeks, 30° C., 12 mm cone [N] | 0.4 | 0.63 | — |
| 4 weeks, 40° C., 12 mm cone [N] | 0.57 | 1.6 | 8.1 |
| 8 weeks, 30° C., 6 mm cone | 0.0 | 0.16 | — |
| 8 weeks, 40° C., 6 mm cone | 0.14 | 0.66 | 1.5 |
| 8 weeks, 30° C., 12 mm cone[N] | 0.21 | 0.51 | — |
| 8 weeks, 30° C., 12 mm cone | 0.33 | 0.99 | 8.0 |

Example 3

Formulation Comprising 5% b.w. TPGS 1000

45 kg water were heated to a temperature of 50° C. 3 kg molten TPGS (Temperature 60° C.) were added under gentle stirring at low intensity (paddle, 250 rpm) and continuous heating (50° C.) with a paddle stirrer. The stirrer was covered by the solution to avoid foaming. After 60 minutes of stirring TPGS was completely dissolved. 154 kg Copovidon solution with a solid content of 37% b.w. were added under gentle stirring. The mixture was stirred for 15 minutes. The solids content was adjusted to 25% b.w. by adding water. The resulting solution was clear and transferred under continuous stirring to the spray granulation apparatus.

Spray granulation was carried out by spouted bed granulation:

| Apparatus | Procell 5 (Glatt) |
|---|---|
| Solid content of the suspension | 25% b.w. |
| Temperature of the gas, inlet | 115° C. |
| Temperature exhaust air | 60° C. |
| Amount of drying gas | 200 m³/h |
| Nozzle gas of the two liquid nozzle | 10 m³/h |
| Flow rate of solution | 5.5 kg/h |

Example 4

Formulation Comprising 20% b.w. TPGS 1000

70 kg water were heated to a temperature of 50° C. 12 kg molten TPGS (Temperature 60° C.) were added under gentle stirring at low intensity (paddle, 250 rpm) and continuous heating (50° C.) with a paddle stirrer. The stirrer was covered by the solution to avoid foaming. After 60 minutes of stirring TPGS was completely dissolved. 130 kg Copovidon solution with a solid content of 37% b.w. were added under gentle stirring. The mixture was stirred for 15 minutes. The resulting solution was clear and transferred under continuous stirring to the spray granulation apparatus.

Spray granulation was carried out by spouted bed granulation:

| Apparatus | Procell 5 (Glatt) |
|---|---|
| Solid content of the solution | 28% b.w. |
| Temperature of the gas, inlet | 105° C. |
| Temperature exhaust air | 60° C. |
| Amount of drying gas | 200 m³/h |
| Nozzle gas of the two liquid nozzle | 12.7 m³/h |
| Flow rate of solution | 3.50 kg/h |

The average particle sizes of the products according to Examples 3 and 4 were measured as described above. The results are depicted in Table III.

TABLE III

| Process | D(0.1) [μm] | D(0.5) [μm] | D(0.9) [μm] | D0(4.3) [μm] |
|---|---|---|---|---|
| Spray Granulation, Ex. 3 | 350 | 492 | 850 | 540 |
| Spray Granulation, Ex. 4 | 370 | 570 | 813 | 562 |

The results of the Cone Penetrometer Test are depicted in the table below. The product containing 5% b.w. of TPGS was not tested, because the firmness of the material is influenced by the TPGS content in the formulation. A product with only 5% b.w. TPGS is at least as stable as a product with 10% b.w. TPGS).

Table IV
Storage Stability, Cone Penetrometer Test, Firmness in [N]

|  | Product with 20% TPGS |
|---|---|
| 10 days, 30° C., 6 mm cone | 0.10 |
| 10 day, 30° C., 12 mm cone | 0.33 |
| 4 weeks, 30° C., 6 mm cone [N] | 0.26 |
| 4 weeks, 40° C., 6 mm cone [N] | 0.43 |
| 4 weeks, 30° C., 12 mm cone [N] | 1.1 |
| 4 weeks, 40° C., 12 mm cone [N] | 2.3 |
| 8 weeks, 30° C., 6 mm cone | 0.42 |
| 8 weeks, 40° C., 6 mm cone | 0.94 |
| 8 weeks, 30° C., 12 mm cone[N] | 0.88 |
| 8 weeks, 30° C., 12 mm cone | 1.63 |

We claim:

1. A storage-stable dust-free homogeneous particulate formulation, consisting of
   (a) at least one water-soluble Vitamin E-derivative,
   (b) at least one hydrophilic polymer,
   (c) optionally additional surface-active substances, and
   (d) optionally additional pharmaceutical additives,
   with the proviso, that the sum of (a), (b), (c) and (d) equals 100% by weight of the formulation, and wherein a fines fraction of the particulate formulation is less than 10% by weight with a particle diameter of less than 100 μm, wherein the particulate formulation is a layered formulation produced by a spray granulation process, and wherein the particulate formulation is solvent-free.

2. The formulation according to claim 1 having an average particle size $D_{0[4,3]}$ of from 300 to 800 μm.

3. The formulation according to claim 1, wherein component (a) is a tocopheryl polyethyleneglycol succinate.

4. The formulation according to claim 1, wherein component (b) is selected from the group consisting of homo- or copolymers of an N-vinyl lactam, cellulose derivatives, polyacrylic polymers, polyalkylene oxides, polyvinyl alcohols and oligo- and polysaccharides.

5. The formulation according to claim 4, wherein component (b) is a homo- or copolymer of an N-vinyl lactam.

6. The formulation according to claim 5, wherein component (b) is a homo- or copolymer of N-vinyl pyrrolidone.

7. The formulation according to claim 6, wherein component (b) is a copolymer of N-vinyl pyrrolidone and vinyl acetate.

8. The formulation according to claim 4, wherein component (b) is a copolymer of N-vinyl caprolactam, vinyl acetate and polyethylene glycol.

9. The formulation according to claim 4, wherein component (b) is a cellulose derivative.

10. The formulation according to claim 1, wherein component (c) is selected from the group consisting of polyalkylene glycol fatty acid esters, polyalkylene glycol fatty alcohol ethers, polyalkylene glycols, poloxamers, polyalkylene glycol glycerides and alkylene glycol fatty acid mono- and diesters.

11. The formulation according to claim 1, wherein component (d) is selected from the group consisting of antioxidants, chelating agents, colorants, flavours, fillers, stabilizers, preservatives and biocides.

12. The formulation according to claim 11, wherein component (d) is ascorbic acid, tocopherol or butyl hydroxyl toluene.

13. The formulation according to claim 1, consisting of
   (a) 5 to 20% by weight of at least one water-soluble Vitamin E-derivative,
   (b) 80 to 95% by weight of at least one hydrophilic polymer,
   (c) 0 to 15% by weight of additional surface-active substances, and
   (d) 0 to 15% by weight of additional pharmaceutical additives.

14. The formulation according to claim 13, consisting of
   (a) 10 to 20% by weight of at least one water-soluble Vitamin E-derivative,
   (b) 80 to 90% by weight of at least one hydrophilic polymer,
   (c) 0 to 15% by weight of additional surface-active substances, and
   (d) 0 to 15% by weight of additional pharmaceutical additives.

15. A spray granulation process for manufacturing the particulate formulation according to claim 1, comprising:
   (i) forming an aqueous solution of components (a), (b) and optionally (c) and (d),
   (ii) atomizing said solution with the help of one or more spray nozzles in an apparatus, and contacting the atomized solution with particulate material consisting of components (a), (b) and optionally (c) and (d),
   (iii) separating a granulated product from fines with a diameter of less than 100 μm particle size, and
   (iv) recirculating the fines into the apparatus.

16. The process according to claim 15, wherein the spray granulation process is a fluidized bed spray granulation process.

17. The process according to claim 15, wherein the aqueous solution has a solids content of from 10 to 50% by weight.

18. The process according to claim 15, wherein step (i) is carried out by blending an aqueous solution of the hydrophilic polymer (b) into an aqueous solution of component (a).

19. The process according to claim 16, wherein the fluidized bed spray granulation process is a spouted bed spray granulation process.

20. The particulate formulation according to claim 13, produced by a spray granulation process comprising:
   (i) forming an aqueous solution of components (a), (b) and optionally (c) and (d),
   (ii) atomizing the solution with the help of one or more spray nozzles and contacting the atomized solution with a fluidized bed of fines of a particulate material consisting of components (a), (b) and optionally (c) and (d),
   (iii) separating a granulated product from fines with a diameter of less than 100 μm particle size, and
   (iv) recirculating the fines into the apparatus.

* * * * *